United States Patent
Ulanch et al.

(10) Patent No.: US 10,514,335 B2
(45) Date of Patent: Dec. 24, 2019

(54) SYSTEMS AND METHODS FOR OPTICAL SPECTROMETER CALIBRATION

(71) Applicant: Arizona Board of Regents on Behalf of the University of Arizona, Tucson, AZ (US)

(72) Inventors: Rachel Nicole Ulanch, Tucson, AZ (US); Richard John Koshel, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 0 days.

(21) Appl. No.: 16/126,512

(22) Filed: Sep. 10, 2018

(65) Prior Publication Data

US 2019/0079004 A1    Mar. 14, 2019

Related U.S. Application Data

(60) Provisional application No. 62/556,032, filed on Sep. 8, 2017.

(51) Int. Cl.
*G01N 21/27* (2006.01)
*G01J 3/51* (2006.01)
(Continued)

(52) U.S. Cl.
CPC .......... *G01N 21/274* (2013.01); *G01J 3/0264* (2013.01); *G01J 3/0272* (2013.01);
(Continued)

(58) Field of Classification Search
CPC ............... G01N 21/274; G01N 21/251; G01N 2201/0616; G01N 2021/3181; G01J 3/524; G01J 3/2803; G01J 3/28; G01J 3/0272; G01J 3/502; G01J 3/51; G01J 3/0264; G01J 3/2823; G01J 2003/2866; G01J 2003/2806

See application file for complete search history.

(56) References Cited

U.S. PATENT DOCUMENTS 7,282,691 B2 * 10/2007 Wilsey .................. G01J 1/44
                                                250/214 R
7,420,663 B2    9/2008 Wang et al.
(Continued)

OTHER PUBLICATIONS

Ulanch, Rachel N. "Replicating the Blue Wool Response Using a Smartphone Spectroradiometer." (2017). (Year: 2017).*

(Continued)

*Primary Examiner* — Dominic J Bologna
(74) *Attorney, Agent, or Firm* — Lathrop Gage LLP

(57) ABSTRACT

Systems and methods spectrally and radiometrically calibrate an optical spectrum detected with a color-image sensor of an optical spectrometer. When the color-image sensor includes a Bayer filter, the red-peaked, green-peaked, and blue-peaked spectral responses of the color filters forming the Bayer filter may be used to identify unique spectral signatures in the red, green, and blue color channels. These spectral signatures may be used to associate calibration wavelengths to the pixel locations of the color-image sensor where the spectral signatures are observed. A fitted model may then be used to associate a wavelength to each pixel location of the color-image sensor. These systems and methods account for translational shifts of the optical spectrum on the color-image sensor induced by optical image stabilization, and thus may aid optical spectrometry utilizing a digital camera in a smartphone or tablet computer.

26 Claims, 12 Drawing Sheets

(51) Int. Cl.
*G01J 3/28* (2006.01)
*G01J 3/02* (2006.01)
*G01J 3/50* (2006.01)
*G01J 3/52* (2006.01)
*G01N 21/25* (2006.01)
*G01N 21/31* (2006.01)

(52) U.S. Cl.
CPC .............. *G01J 3/28* (2013.01); *G01J 3/2803* (2013.01); *G01J 3/2823* (2013.01); *G01J 3/502* (2013.01); *G01J 3/51* (2013.01); *G01J 3/524* (2013.01); *G01N 21/251* (2013.01); *G01J 2003/2806* (2013.01); *G01J 2003/2866* (2013.01); *G01N 2021/3181* (2013.01); *G01N 2201/0616* (2013.01)

(56) References Cited

U.S. PATENT DOCUMENTS

| | | | | |
|---|---|---|---|---|
| 8,761,504 B2* | 6/2014 | Hirakawa | ............. | G06T 1/0007 348/273 |
| 8,780,356 B1* | 7/2014 | Saari | ......................... | G01J 3/45 356/454 |
| 9,215,984 B2* | 12/2015 | Hattery | ................. | A61B 5/0059 |
| 2010/0201981 A1* | 8/2010 | Stanke | ....................... | G01J 3/02 356/328 |
| 2014/0104465 A1* | 4/2014 | Yamashita | ............. | H04N 9/045 348/280 |
| 2016/0328848 A1* | 11/2016 | Andre | .................... | G06T 7/0012 |
| 2018/0010966 A1* | 1/2018 | Ichikawa | ................. | H04N 9/04 |

OTHER PUBLICATIONS

Debevec et al. (1997) "Recovering high dynamic range radiance maps from photographs," In *Proceedings of the 24th annual conference on Computer graphics and interactive techniques* (SIGGRAPH '97). ACM Press/Addison-Wesley Publishing Co., New York, NY, USA, pp. 369-378.

Hossain et al. (2016) "Optical fiber smartphone spectrometer," Optics Letters, vol. 41, Issue 10, pp. 2237-2240.

* cited by examiner

SYSTEMS AND METHODS FOR OPTICAL SPECTROMETER CALIBRATION

RELATED APPLICATIONS

This application claims priority to U.S. Provisional Patent Application Ser. No. 62/556,032, filed Sep. 8, 2017, which is incorporated herein by reference.

BACKGROUND

A blue wool fading test is a light comparative fading test from the textile industry that was adopted by the art conservation community in the 1960s. This technique was regarded as a cost effective, readily available comparative standard for understanding lightfastness of museum objects, but not an end-all solution. Other solutions have been found since the suggestion of the blue wool standard, such as the Canadian Light Damage Calculator and Lightcheck® comparator guides for lighting museum objects. Another solution is the Berlin model for comparing tested spectral data, which requires expensive equipment. Yet another solution is microfadeometry, which directly tests the object with a focused xenon source that disadvantageously deteriorates the artwork. None of these methods has been able to completely replace the vetted, cost effective, easy-to-use blue wool standard for determining the sensitivity of museum and gallery objects.

SUMMARY OF THE EMBODIMENTS

In an embodiment, an optical spectrometer for use with a smartphone is configured to measure the illumination and reflectance spectrum of museum and gallery objects to deduce an absorption spectrum that may be correlated to an expected blue wool response under the same conditions. The optical spectrometer includes an optical-assembly attachment made from off-the-shelf and 3D-printed parts. Embodiments disclosed herein measure the deterioration of blue wool under a high intensity source and may predict the expected time for a blue wool specimen to visibly fade under the illumination of museum LED lighting.

In an embodiment, a process spectrally and radiometrically calibrates a smartphone-based optical spectrometer to provide absolute spectral radiometric measurements. Current technology usually provides relative spectral measurements of dispersive spectrums provided using a spectrometer, similar to what is discussed in U.S. Pat. No. 7,420,663. However, processes disclosed herein are not limited to mobile/smartphone attachments and may be implemented with any optical system that disperses light into a spectrum and measures the spectrum with an image detector. Such systems may include spectrometers, spectroradiometers, and spectrophotometers.

In an embodiment, a calibration technique calibrates the absolute radiance using chromaticity coordinates, which are unique to an optical design, and measurements of the spectrum of the sun. Using the chromaticity coordinates and measuring the sun provides a broad spectrum that locates unique identifying features of the chromaticity space in pixel and wavelength space. The broad spectrum allows the measured data to be calibrated radiometrically by comparison to measured data of the sun and atmosphere that are found from atmospheric and circumsolar radiometric modeling software utilizing radiometric data taken around the United States of America.

Embodiments herein may be useful for a digital camera system (e.g., smartphone, tablet, digital SLR camera) that utilizes a hardware-driven optical image stabilizer (OIS) to stabilize the image on the detector plane in response to mechanical jitter.

Applications of methods and systems disclosed herein are not limited to absolute radiometric measurements but could also replace the process of using color cards for photographic color matching. By using the chromaticity coordinate system, the exact wavelength within an error margin, may be calculated and adjusted.

Embodiments disclosed herein enhance dynamic range by using a high dynamic range (HDR) algorithm. However, the requirement is that the system be able to provide a dynamic range of around $10^5$ or even $10^8$ with better understanding of the nonlinear response of the detector being used. Currently smartphone/mobile phone spectrometers are shown to provide around $10^2$ dynamic range, and spectrometers with the $10^5$ dynamic range are expensive.

In one embodiment, a method that calibrates a color-image sensor for optical spectrometry includes a step that detects an optical spectrum with the color-image sensor. The color-image sensor has an image sensor overlaid with a color filter array such that each of a plurality of pixels of the color-image sensor has one of a first spectral response, a second spectral response, and a third spectral response. The method also includes a step that determines a first pixel location of the color-image sensor where a first color channel signal, formed from the pixels having the first spectral response, equals a second color channel signal formed from the pixels having the second spectral response. The method also includes a step that determines a second pixel location of the color-image sensor where the second color channel signal equals a third color channel signal formed from the pixels having the third spectral response. The method also includes steps that associate the first pixel location with a first calibration wavelength, and associate the second pixel location with a second calibration wavelength.

In another embodiment, a spectrum recording system includes a color-image sensor formed from an image sensor overlaid with a color filter array such that each of a plurality of pixels of the color-image sensor has one of a first spectral response, a second spectral response, and a third spectral response. The spectrum recording system further includes at least one processor, and memory communicatively coupled to the at least one processor and the color-image sensor. The spectrum recording system also includes machine-readable instructions stored in the memory and configured to control the at least one processor to: (i) for each of the pixels, store in the memory one pixel value representing an electrical response of said each of the pixels to an optical spectrum detected with the color-image sensor; (ii) form a first color channel signal, a second color channel signal, and a third color channel signal from the pixel values obtained from the pixels having the first spectral response, second spectral response, and third spectral response, respectively; (iii) determine a first pixel location where the first color channel signal equals the second color channel signal; (iv) determine a second pixel location where the second color channel signal equals the third color channel signal; (v) associate the first pixel location with a first calibration wavelength; and (vi) associate the second pixel location with a second calibration wavelength.

In another embodiment, a method that calibrates a color-image sensor for optical spectrometry includes a step that detects an optical spectrum with the color-image sensor. The color-image sensor has an image sensor overlaid with a color filter array such that each of a plurality of pixels of the color-image sensor has one of several spectral responses. The method also includes a step that determines a plurality of pixel locations of the color-image sensor where, for each of the pixel locations, a color channel signal formed from pixels having one spectral response equals a second color channel signal formed from pixels having another spectral response. The method also includes a step that associates each of the pixel locations with a calibration wavelength.

DETAILED DESCRIPTION OF THE EMBODIMENTS

Figure 1:
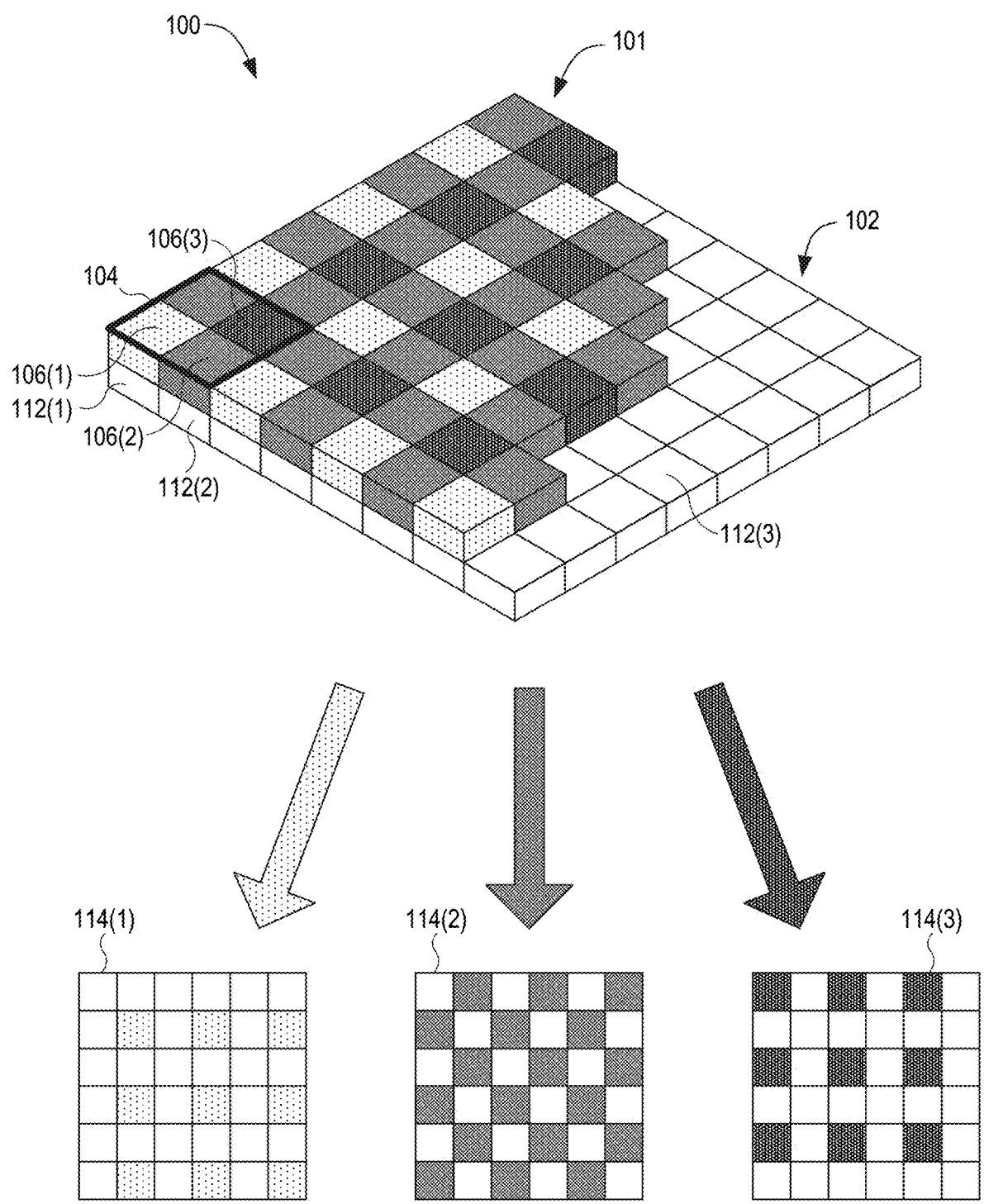
FIG. 1 shows a color-image sensor formed from an image sensor overlaid with a Bayer filter.

Increase in smartphone ownership and use has led to advances in measurement and analysis techniques that utilize a smartphone's camera. Current smartphone technology allows a user to capture high-resolution images at a fraction of the cost of comparable instruments. With the camera being one of the more expensive and advanced pieces of technology on a smartphone, many smartphone attachments have been developed to leverage the capabilities of these widely available imaging devices. Many of these attachments have been developed in the fields of biology and chemistry with the goal of bringing advanced medical care and testing to remote locations. Other recent advances have focused on non-medical types of diagnostics and testing.

A smartphone spectrometer is described by Md Arafat Hossain, John Canning, Kevin Cook, and Abbas Jamalipour in "Optical fiber smartphone spectrometer" *Optics Letters* vol. 41, issue 10, pp. 2237-2240 (2016). Designed for food quality monitoring, the system, like most smartphone spectrometers, includes optics, a reflective diffraction grating, and a cylindrical lens. The system also uses a fiber bundle for illumination and collection of light. However, the spectral bandwidth was limited to the range of 420 to 670 nm, and the diffraction grating, chosen for cost effectiveness, limited the spectral resolution. Other limitations arose from the unreliability of the smartphone's internal RGB map to color space, meaning that results may have errors due to the smartphone's internal color space mapping function and the 8-bit resolution of the jpg file format. The whole system is bulky due to the path length needed for the reflective dispersion, the illumination source, and the mechanical mounting of the fiber bundle. Thus, the design lacks features, including spectral bandwidth, resolution and footprint, needed by several communities, like art conservationists.

A spectrometer has also been built into the Changhong H2 smartphone. Currently there is limited data on the system, however some articles have described it as a spectrometer that measures the reflections of an object being illuminated by an onboard infrared source to determine the molecular makeup of the object. The data collected is compared to a database of known spectra accessed on the cloud, to identify the object being probed. The infrared source can provide relative spectral measurements of the object but cannot provide the radiometric measurements that are important in museum and gallery settings. The H2 smartphone spectrometer also lacks pointing control. The aperture is on the back of the phone, and an object must be close enough to the aperture and source so that enough light reflects back into the aperture for sensing. While the H2 addresses ease of use because the system is already assembled, it is not useful to art conservationists conducting in situ light sensitivity measurements of an object because the method relies on an infrared source for absorption and/or reflective spectroscopy.

More cost-effective smartphone spectrometers have been developed, but are constrained to lower resolutions, their purpose being usually directed toward education and providing advanced science technology to remote communities. These systems are often unable to provide useful measurement data. Public Labs, a nonprofit organization, designed a cardboard tube with a slit that can be attached to a phone that uses a transmissive piece of diffraction material (e.g., a compact disc) as the spectrometer attachment. However, the only field control, one of the main factors controlling resolution, is the slit at the front of the cardboard tube translating to poor system resolution. Thus, Public Lab's system educates and allows researchers to work remotely, but with performance limitations.

There are two key differences between the cameras used in smartphones and those used in high-end optical spectrometers designed for the scientific community. First, a smartphone camera uses a color filter array superimposed over the image sensor to record color information. The color filter array affects intensity/power calibration by changing the spectral response of the image sensor. However, these changes in spectral response may be accounted for with radiometric calibration.

Second, many smartphones utilize an optical image stabilizer (OIS) that mechanically moves the camera lens (or lens assembly) in response to mechanical motion of the system (e.g., hand jitter, wind, and walking motion). While an OIS advantageously allows a user of a smartphone to record a video with minimal blurring, for a smartphone spectrometer an OIS disadvantageously pivots the lens in front of the image sensor, shifting the location of the image on a detector plane of the image sensor. When the image shifts, so does the relationship between pixel position (i.e., row, column) of the image sensor and wavelength, thus requiring the wavelength response of the smartphone spectrometer to be recalibrated. This disadvantage is particularly challenging to overcome for smartphones having an OIS that cannot be disabled. Examples of shifting spectral images are discussed in more detail below with regards to FIG. 3.

FIG. 1 shows a color-image sensor 100 formed from an image sensor 102 overlaid with a Bayer filter 101. Bayer filter 101 is formed from a plurality of color filter elements 106 arranged in a repeating submosaic 104. Each color filter element 106 is one of a red-transmitting filter 106(1), a green-transmitting filter 106(2), and a blue-transmitting filter 106(3). Each of color filter elements 106 is superimposed over one of a plurality of sensor pixels 112 of image sensor 102. Without Bayer filter 101, each of sensor pixels 112 has an identical spectral response. When Bayer filter 101 is superimposed on image sensor 102, each of sensor pixels 112 has a spectral response determined in part by the corresponding color filter element disposed over it. More specifically, each of sensor pixels 112 is one of a red-sensing pixel 112(1), a green-sensing pixel 112(2), and a blue-sensing pixel 112(3). The electrical outputs of all red-sensing pixels 112(1) may be grouped together into a red channel signal 114(1), the electrical outputs of all green-sensing pixels 112(2) may be grouped together into a green channel signal 114(2), and the electrical outputs of all blue-sensing pixels 112(3) may be grouped together into a blue channel signal 114(3).

Figure 2:
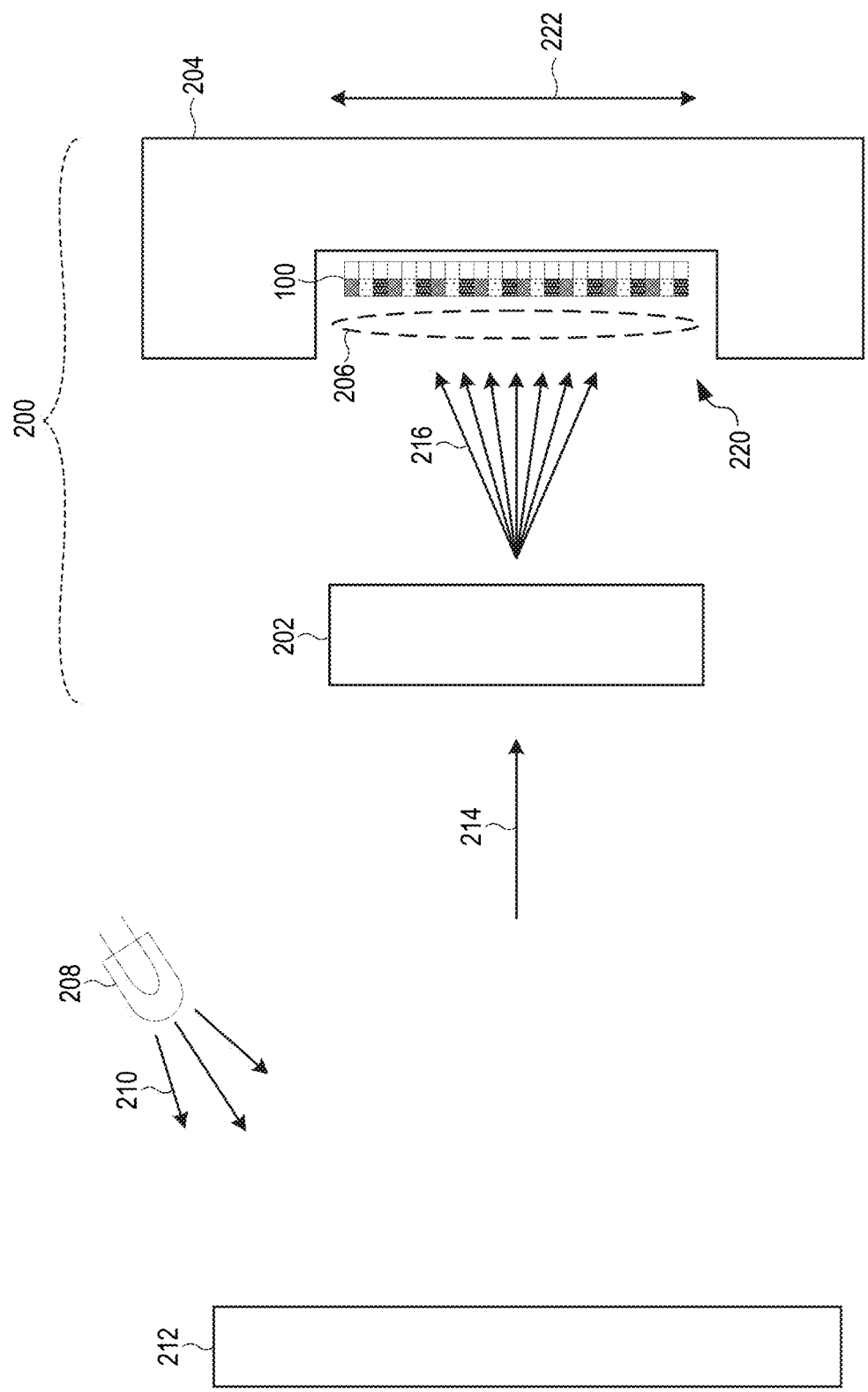
FIG. 2 shows one example of a smartphone spectrometer measuring spectral components of input light with the color-image sensor of FIG. 1, in embodiments.

FIG. 2 shows one example of a smartphone spectrometer 200 measuring spectral components of input light 214 with color-image sensor 100 of FIG. 1. Smartphone spectrometer 200 includes a smartphone 204 having a camera 220, and a spectrometer optics 202 that disperse input light 214 into an optical spectrum 216. Camera 220 includes color-image sensor 100 and a lens 206. In some embodiments, camera 220 operates without lens 206, wherein color-image sensor 100 directly detects optical spectrum 216 without focusing. While FIG. 2 shows input light 214 being collected by free-space spectrometer optics 202, spectrometer optics 202 may also include fiber-optics that collect input light 214 and/or deliver input light 214 to other elements of spectrometer optics 202 that disperse input light 214.

Optical spectrum 216 is formed from spectral components of input light 214, each spectral component having one wavelength or range of wavelengths. Spectrometer optics 202 generate optical spectrum 216 by dispersing input light 214 along a dispersion direction 222. Thus, optical spectrum 216 is projected onto color-image sensor 100 such that there is a correlation between wavelength and a pixel position of color-image sensor 100. For simplicity, dispersion direction 222 may be aligned with one of the two principal axes of color-image sensor 102. For example, dispersion direction 222 may be chosen such that wavelength of optical spectrum 216 varies with a pixel row of color-image sensor 100, in which case the pixel position is the pixel row. Alternatively, dispersion direction 222 may be chosen such that wavelength of optical spectrum 216 varies with a pixel column of color-image sensor 100, in which case the pixel position is the pixel column. Spectrometer optics 202 may include any optic(s) known to disperse light, such as one or more dispersive prism, and one or more diffraction grating (either transmissive or reflective).

In FIG. 2, smartphone spectrometer 200 is shown measuring input light 214 reflecting off of a test object 212 illuminated with source light 210 emitted from an optical source 208. For example, test object 212 may be a work of art in a gallery, such as a painting, in which case source light 210 is broadband light and optical source 208 is one or more of a lamp, light bulb, and LED light source. In one embodiment, test object 212 is paint having a color profile measured by smartphone spectrometer 200 so as to identify a matching paint. Test object 212 may be outside, in which case source light 210 may be sunlight. In some embodiments, smartphone spectrometer 200 is used to directly measure spectral components of source light 210 and/or compare these spectral components to those of input light 214 reflecting off of test object 212. In this manner of operation, an absorption spectrum of test object 212 may be obtained.

Smartphone 204 may operate camera 220 to capture an image of optical spectrum 216, thereby recording pixel values of the pixels of color-image sensor 100. To accurately identify wavelengths of optical spectrum 216, a wavelength calibration may be performed to map each pixel position (e.g., each pixel row or pixel column of image sensor 102) into a wavelength, or range of wavelengths.

Figure 3:
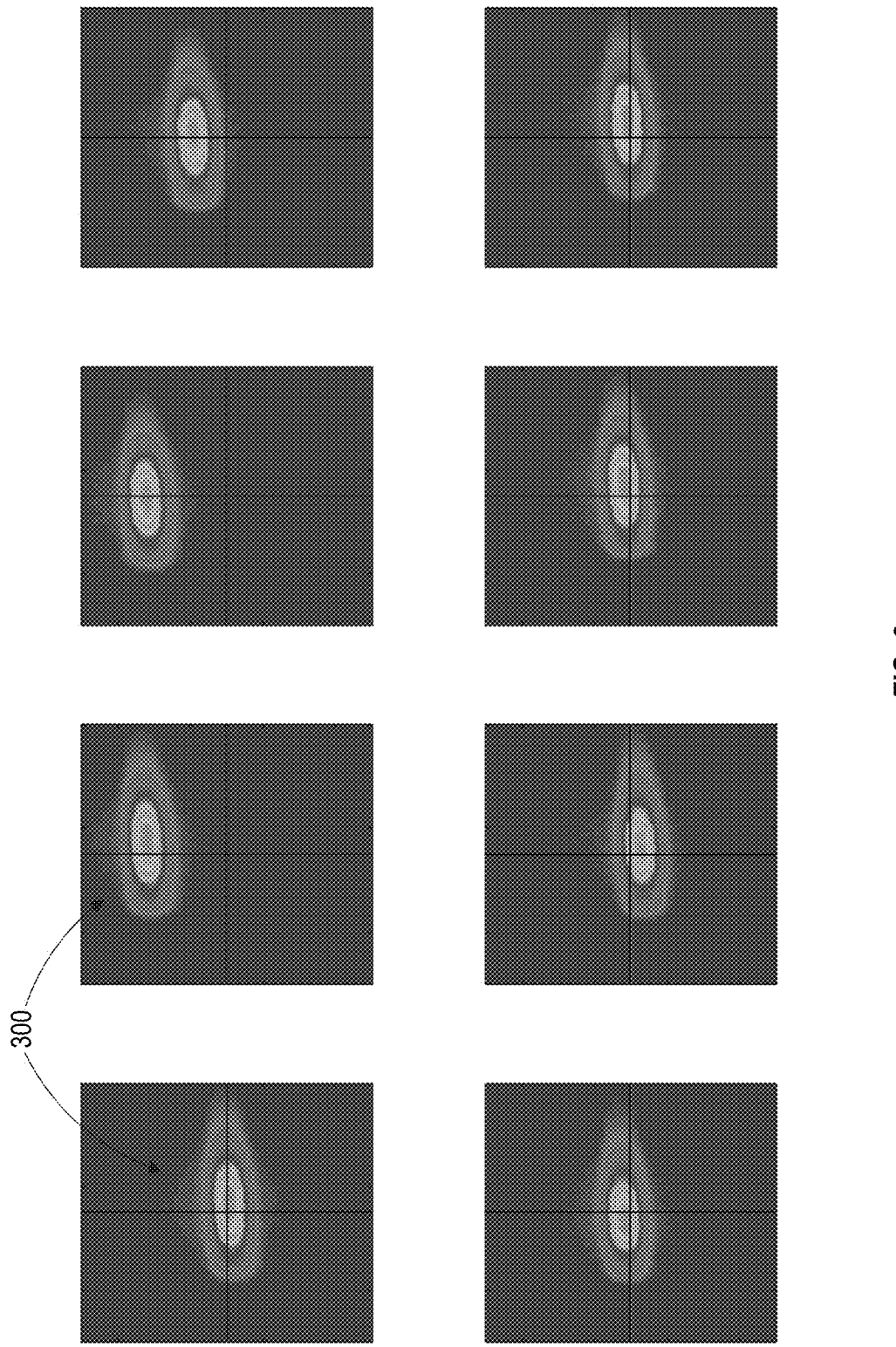
FIG. 3 is a series of eight images showing an optical spectrum shifting on a detector plane of a color-image sensor due to optical image stabilization.

FIG. 3 is a series of eight images showing an optical spectrum 300 shifting on a detector plane of a color-image sensor due to optical image stabilization. The images were obtained with a camera spectrometer according to the example usage shown in FIG. 2. More specifically, color-image sensor 100 was a Sony IMX260 CMOS color-image sensor forming part of a rear-facing camera of a Samsung Galaxy S7 smartphone. The smartphone was mounted on a tripod so as to remain stationary, and each of the eight images in FIG. 3 displays the same range of pixel rows and columns. A lens in front of the CMOS image sensor (e.g., lens 206 of FIG. 2) was actively moved by the smartphone, as part of optical image stabilization, between images. As a result, optical spectrum 300 shifts in both directions by up to one hundred pixels. For clarity, crosshairs have been centered on each image to aid the eye. Optical spectrum 300 was obtained from sunlight (e.g., source light 210) reflecting off a sample of blue wool, which is an example of test object 212.

Figure 4:
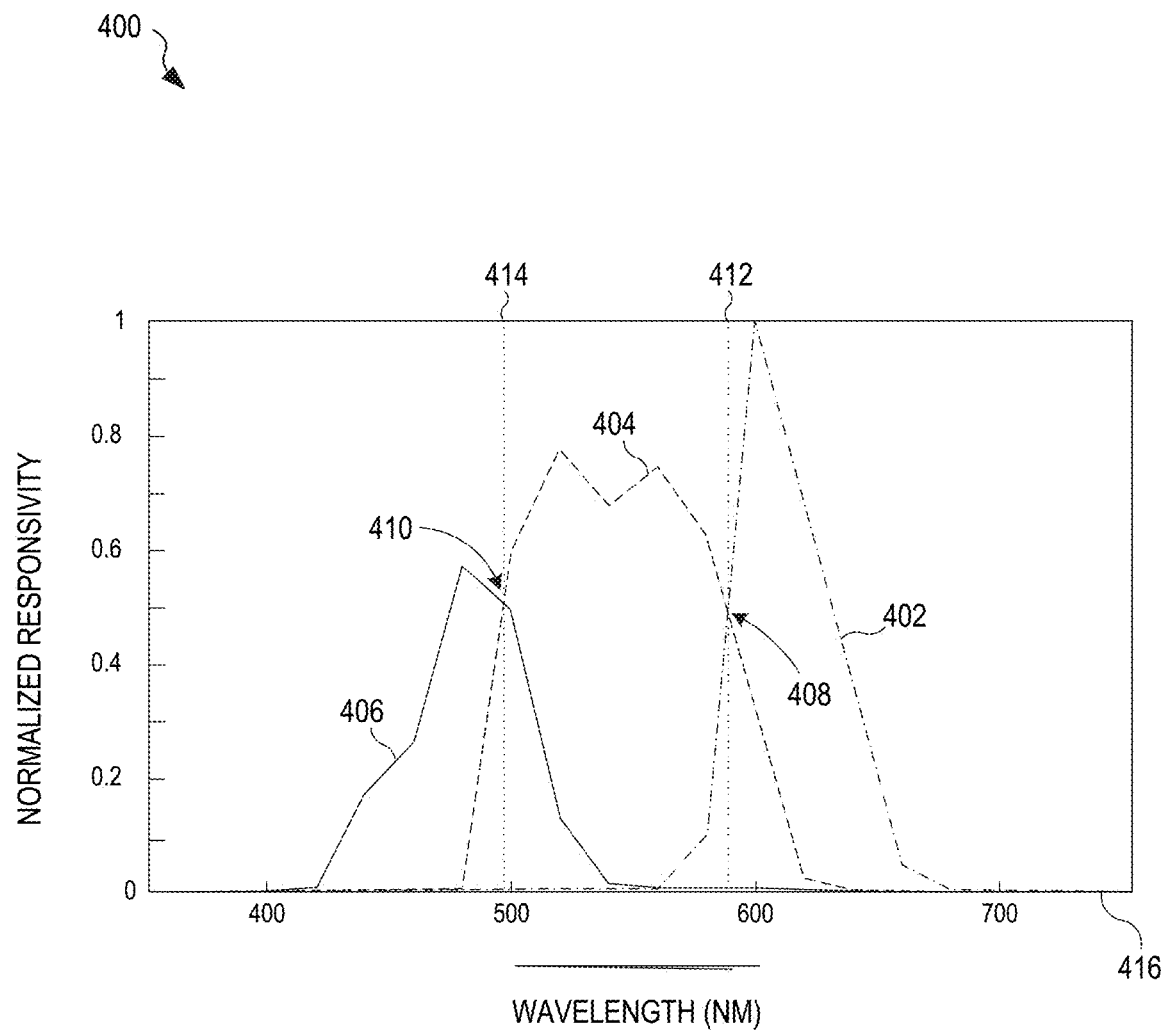
FIG. 4 is a plot showing normalized responsivities, as a function of wavelength, for a color-image sensor.

FIG. 4 is a plot 400 showing normalized responsivities, as a function of wavelength, for a color-image sensor. FIG. 4 shows a first spectral response 402 (dashed-dotted line) corresponding to red-sensing pixels 112(1), a second spectral response 404 (dashed line) corresponding to green-sensing pixels 112(2), and a third spectral response 406 (solid line) corresponding to blue-sensing pixels 112(3). Spectral responses 402, 404, and 406 were obtained from measurements of the Sony IMX260 CMOS color-image sensor discussed above, and thus combine the inherent responsivity of sensor pixels 112 with the different transmissions of red-transmitting filter 106(1), green-transmitting filter 106(2), and blue-transmitting filter 106(3). As shown in FIG. 4, first spectral response 402 and second spectral response 404 cross at a first crossing point 408 occurring at a first wavelength. The first wavelength may be determined from where a line 412 intersects an x-axis 416 of plot 400. Similarly, second spectral response 404 and third spectral response 406 cross at a second crossing point 410 occurring at a second wavelength. The second wavelength may be determined from where a line 414 intersects x-axis 416. In the example of FIG. 4, the first wavelength is at 590 nm, and the second wavelength is at 495 nm.

One aspect of the present embodiments is the realization that crossing points 408 and 410 may be used to calibrate the wavelength-response of a smartphone spectrometer directly from images recorded by the camera. Since each image includes enough information to calibrate wavelength, shifting of an optical spectrum on the detector plane by an OIS no longer affects wavelength accuracy. The first wavelength indicated in plot 400 by line 412 may be referred to herein as "the first calibration wavelength" and the second wavelength indicated by line 414 may be referred to herein as "the second calibration wavelength."

When smartphone spectrometer 200 receives a broadband input light 214 to excite red-sensing pixels 112(1), green-sensing pixels 112(2), and blue-sensing pixels 112(3), a first pixel location of color-image sensor 100 may be identified from where a red channel signal and a green channel signal cross. This first pixel location may be associated with the first calibration wavelength. Similarly, a second pixel location of color-image sensor 100 may be identified from where the green channel signal and a blue channel signal cross. This second pixel location may be associated with the second calibration wavelength. A wavelength for each other pixel location may then be determined by fitting the first pixel location, first calibration wavelength, second pixel location, and second calibration wavelength to a fitted model. For example, the first pixel location, first calibration wavelength, second pixel location, and second calibration wavelength may be fit to a line using linear regression; the line may then be used to (a) determine the pixel location for a given wavelength, and (b) determine the wavelength for a given pixel location.

With the fitted model, features in the optical spectrum may be accurately assigned a wavelength or range of wavelengths. For example, a peak in the optical spectrum may be identified with a center pixel position and/or a width in units of pixels. The fitted model may be used to convert the center pixel position into a center wavelength of the peak, and to convert the width in pixels to a width in units of wavelength (e.g., nanometers).

It should be appreciated that every pixel position (e.g., pixel row, pixel column) of color-image sensor 100 is missing one of red-sensing pixels 112(1) and blue-sensing pixels 112(3). Thus, to assign a value to the red spectral response for a pixel position missing red-sensing pixels 112(1), interpolation of neighboring red-sensing pixels 112(1) may be used. Similarly, to assign a value to the blue spectral response for a pixel position missing blue-sensing pixels 112(3), interpolation of neighboring red-sensing pixels 112(3) may be used. For a Bayer filter 100, every pixel row and column contains green-sensing pixels 112(2).

The red, green, and blue spectral responses of color-image sensor 100 must be known to identify the first and second calibration wavelengths. To measure the spectral responses, any one of several techniques may be used. For example, optical spectrum smartphone spectrometer 200 may be illuminated with narrow-band light of a known power/intensity and wavelength. The light may be generated by a reference lamp and filtered by a calibrated spectroradiometer. The electrical response of color-image sensor 100 to the narrow-band light may be compared to the known power of the narrow-band light to determine a responsivity for each color channel of color-image sensor 100 at the known wavelength. Alternatively, red, green, and blue spectral responses of color-image sensor 100 may be obtained from a color matrix in meta data of a file storing an image obtained with color-image sensor 100.

Similar radiometric calibration techniques may be implemented with smartphone spectrometer 200 such that smartphone spectrometer 200 acts as a smartphone spectroradiometer that accurately measures a radiometric value (e.g., power) for each detected spectral component. Thus, the smartphone spectroradiometer is calibrated both spectrally and radiometrically. In one embodiment, smartphone spectrometer 200 is radiometrically calibrated by measuring optical spectrum 216 of sunlight directed into smartphone spectrometer 200 as input light 214. The resulting color-channel signals form a measured irradiance spectrum that may be compared to a modeled irradiance spectrum of the sunlight to generate one or more radiometric calibration factors. These radiometric calibration factors may be subsequently used to radiometrically correct other measured spectra.

Figure 5:
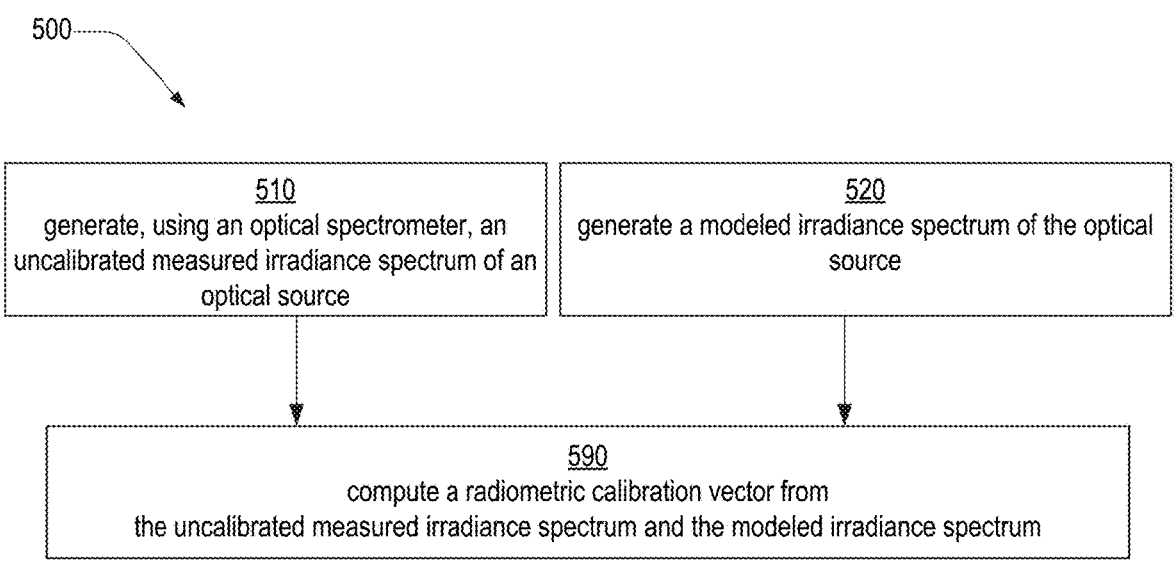
FIG. 5 is a flowchart illustrating one example method that radiometrically calibrates an optical spectrometer, in an embodiment.

FIG. 5 is a flowchart illustrating one example method 500 that radiometrically calibrates an optical spectrometer. Method 500 may be implemented with smartphone spectrometer 200 of FIG. 2. Method 500 includes steps 510, 520, and 590. Step 510 generates, using the optical spectrometer, an uncalibrated measured irradiance spectrum of an optical source (e.g., optical source 208 of FIG. 2). The uncalibrated measured irradiance spectrum may be generated, for example, from pixel values recorded from a color-image sensor (e.g. color-image sensor 100 of FIG. 1). The optical source may be any light source with a known emission spectrum, for example, at wavelengths spanning from ultraviolet to near-infrared electromagnetic radiation. Step 520 generates a modeled irradiance spectrum of the optical source. Step 590 computes a radiometric calibration vector from the uncalibrated measured irradiance spectrum and the modeled radiance spectrum, the radiometric calibration vector having a plurality of radiometric calibration factors.

Figure 6:
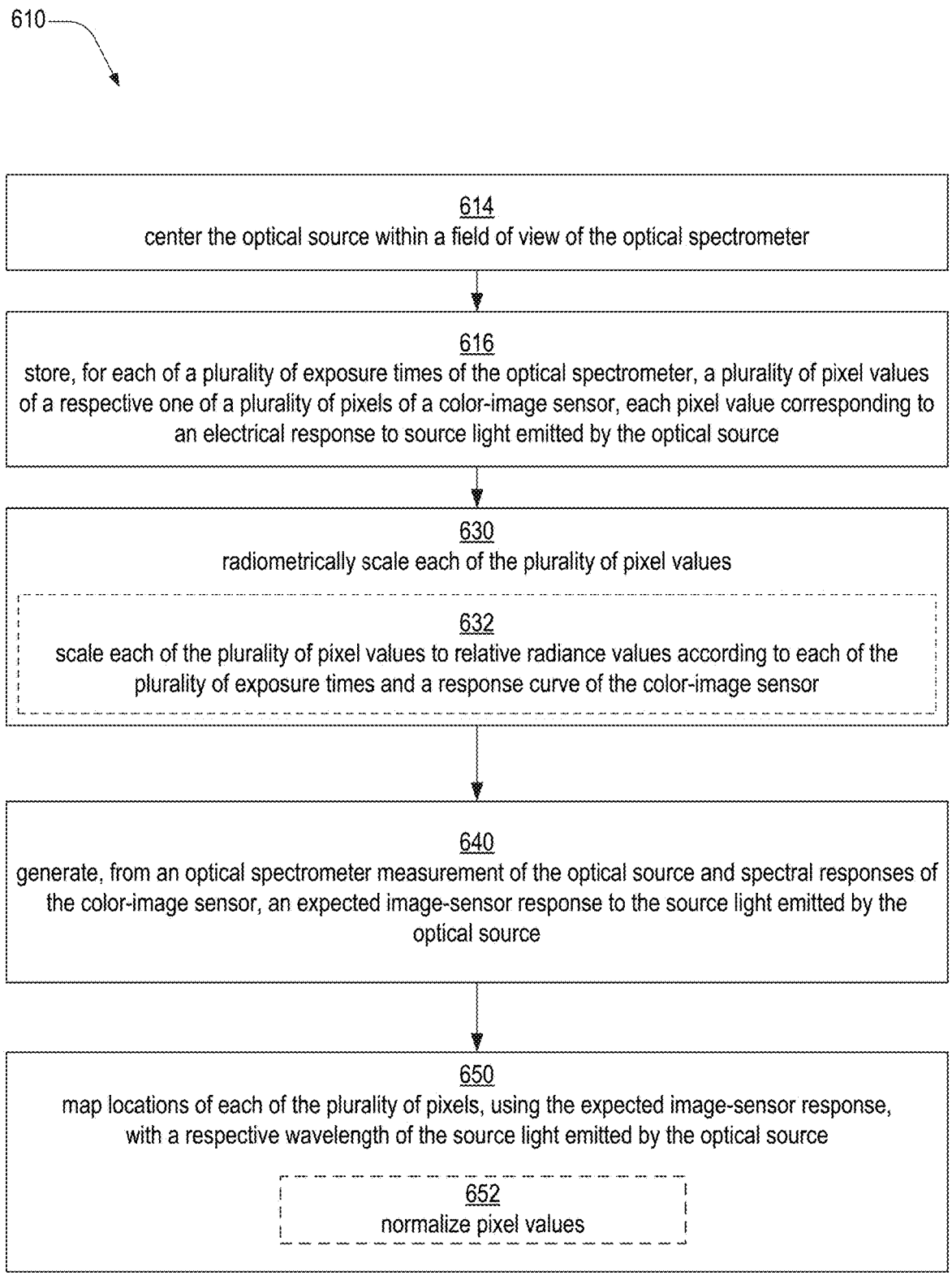
FIG. 6 is a flowchart illustrating one example method that generates, using an optical spectrometer, a calibrated measured irradiance spectrum of an optical source, in an embodiment.

FIG. 6 is a flowchart illustrating one example method 610 that generates, using an optical spectrometer, a calibrated measured irradiance spectrum of source light emitted by an optical source. Method 610 may be implemented with smartphone spectrometer 200 of FIG. 2. Method 610 is an example of step 510 of method 500, and includes steps 614, 616, 630, 640, and 650. Step 614 centers the optical source (e.g., optical source 208 of FIG. 2) within a field of view of the optical spectrometer. Step 616 stores, for each of a plurality of exposure times of the optical spectrometer, a plurality of pixel values of a respective one of a plurality of pixels of a color-image sensor of the optical spectrometer, each pixel value corresponding to an electrical response to the optical spectrum of the source light. Step 630 radiometrically scales each of the plurality of pixel values. In one example, step 630 radiometrically scales the plurality of pixel values using the radiometric calibration vector generated by step 590 of method 500. Step 640 generates, from an optical spectrometer measurement of the optical source and spectral responses of the color-image sensor, an expected image-sensor response to the optical source. Step 650 maps locations of each of the plurality of pixels, using the expected image-sensor response, with a respective wavelength of the source light. Step 650 may include a step 652 that normalizes the pixel values. Step 630 may include a step 632 that scales each of the plurality of pixel values to relative radiance values according to each of the plurality of exposure times and a response curve of the color-image sensor.

Figure 7:
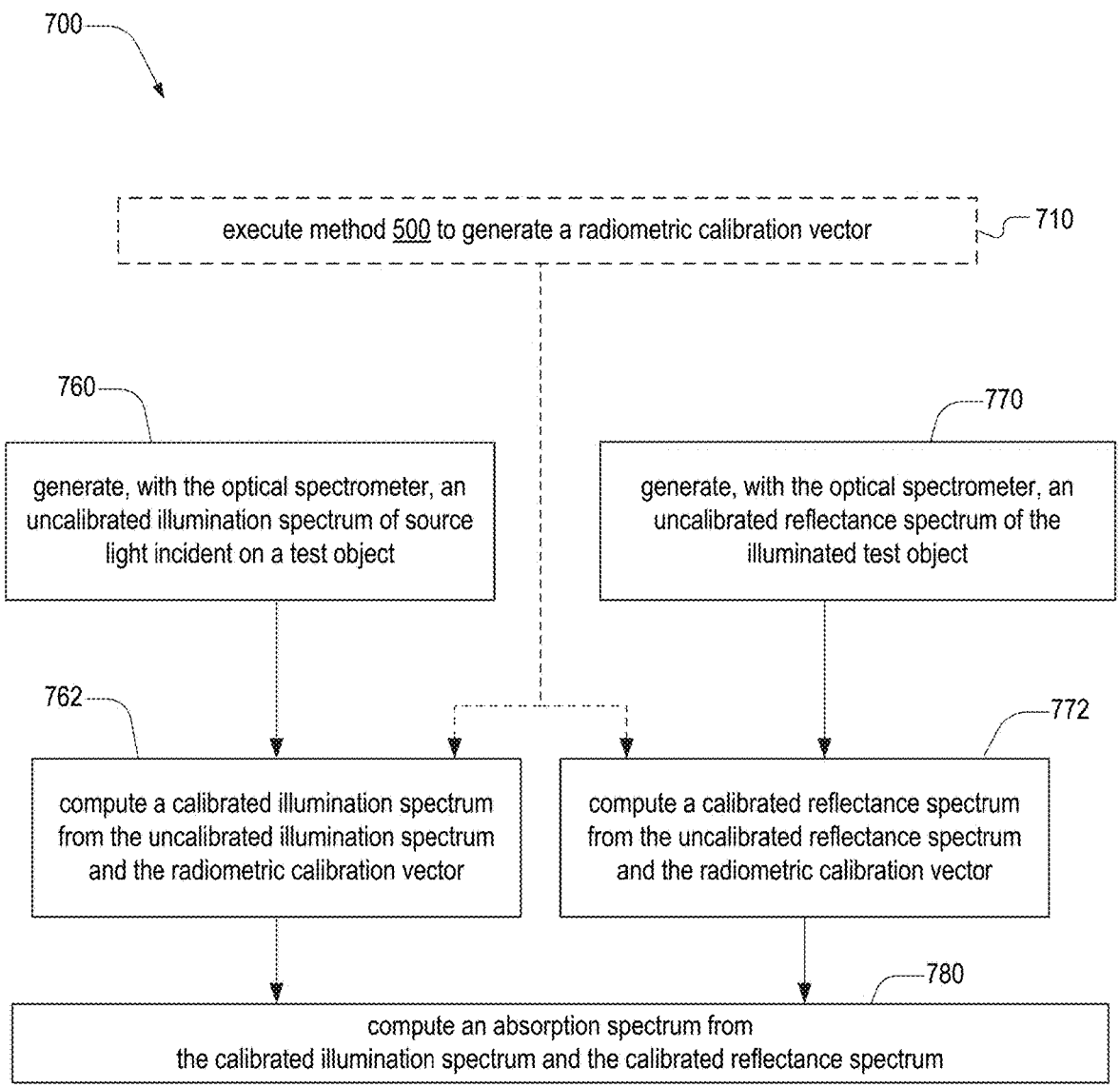
FIG. 7 is a flowchart illustrating one example method that measures, using an optical spectrometer, an absorption spectrum of a test object, in an embodiment.

FIG. 7 is a flowchart illustrating one example method 700 that measures, using an optical spectrometer, an absorption spectrum of a test object. Method 700 may be implemented with smartphone spectrometer 200 of FIG. 2. Method 700 includes steps 760, 762, 770, 772, and 780. In one embodiment, method 700 further includes a step 710 that executes method 500 to generate a radiometric calibration vector. Step 760 generates, with the optical spectrometer, an uncalibrated illumination spectrum of source light (e.g., source light 210 of FIG. 2) incident on the test object (e.g., test object 212 of FIG. 2). Step 762 computes a calibrated illumination spectrum from the uncalibrated illumination spectrum and the radiometric calibration vector. Step 770 generates, with the optical spectrometer, an uncalibrated reflectance spectrum of the illuminated test object. Step 772 computes a calibrated reflectance spectrum from the uncalibrated reflectance spectrum and the radiometric calibration vector. Step 780 computes an absorption spectrum from the calibrated illumination spectrum and the calibrated reflectance spectrum.

Figure 8:
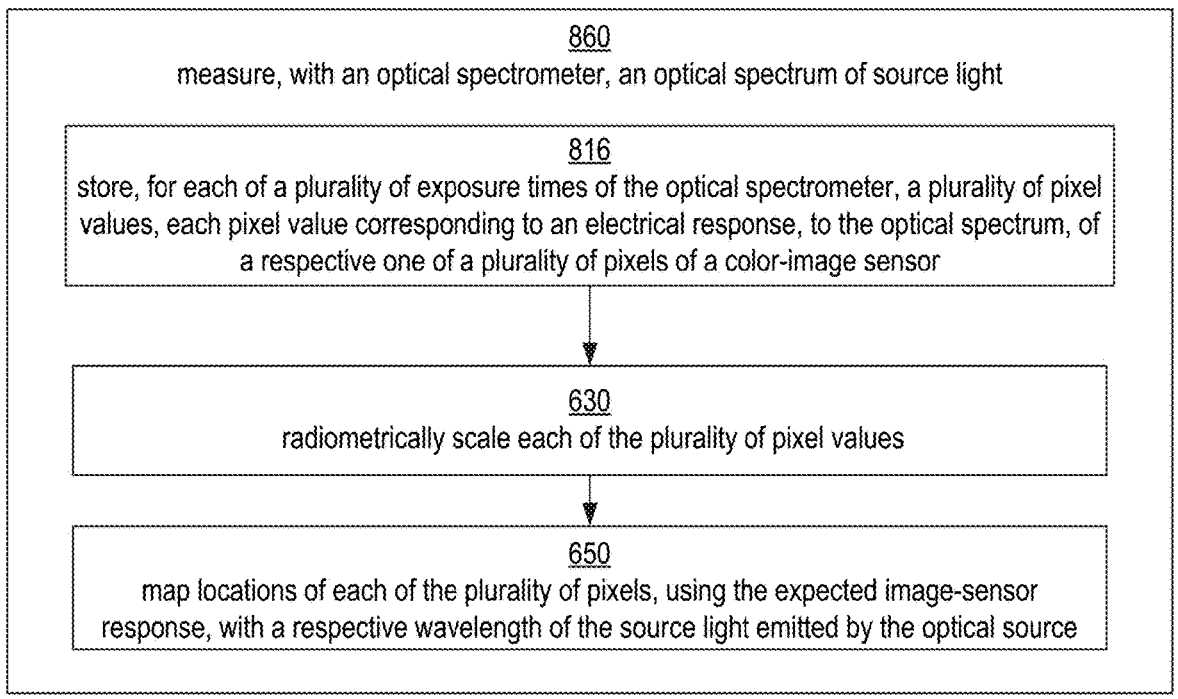
FIG. 8 is a flowchart illustrating one example method that measures, using an optical spectrometer, an optical spectrum of source light, in an embodiment.

FIG. 8 is a flowchart illustrating one example method 860 that measures, with an optical spectrometer, an optical spectrum of source light. Method 860 may be implemented with smartphone spectrometer 200 of FIG. 2. Method 860 is an example of step 760 of method 700, and includes step 816, step 630 of method 610, and step 650 of method 610, where the optical source emits the source light (e.g., optical source 208 of FIG. 2 emits source light 210). Step 816 stores, for each of a plurality of exposure times of the optical spectrometer, a plurality of pixel values, each pixel value corresponding to an electrical response, to the optical spectrum of the source light, of a respective one of a plurality of pixels of a color-image sensor. Step 816 is one example of step 616 of method 610.

Figure 9:
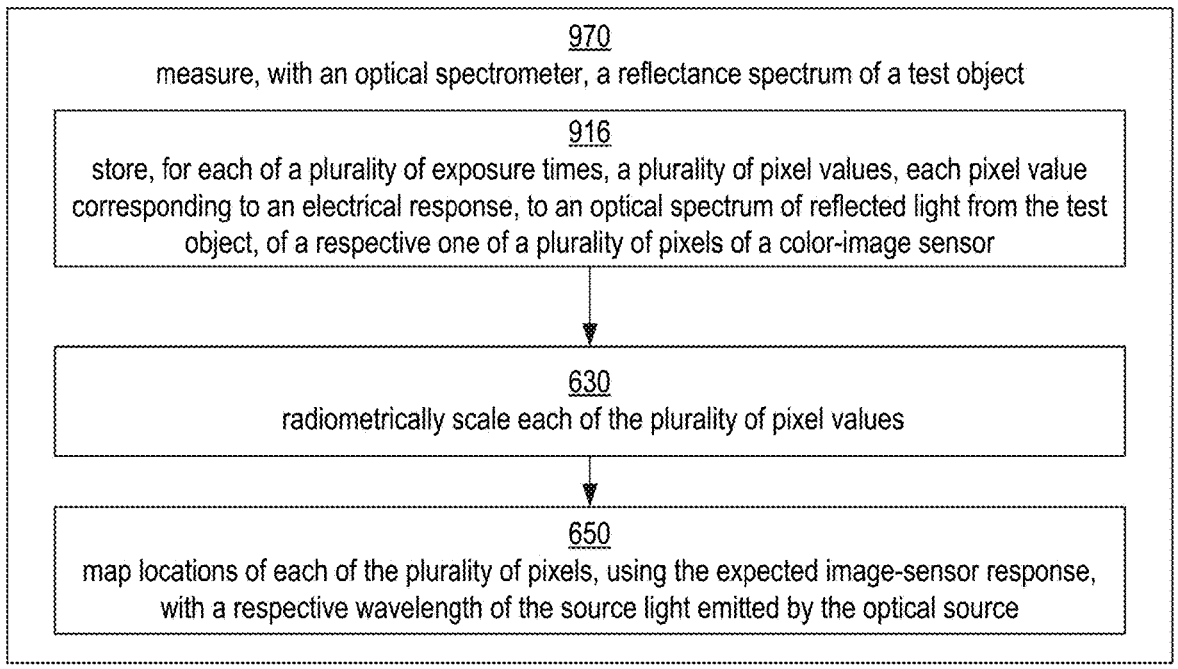
FIG. 9 is a flowchart illustrating one example method that measures, with an optical spectrometer, a reflectance spectrum of a test object, in an embodiment.

FIG. 9 is a flowchart illustrating one example method 970 that measures, with an optical spectrometer, a reflectance spectrum of a test object. Method 970 may be implemented with smartphone spectrometer 200 of FIG. 2. Method 970 is an example of step 770 of method 700, and includes step 916, step 630 of method 610, and step 650 of method 610, where the optical source emits the source light reflected by the test object as reflected light. Step 216 stores, for each of a plurality of exposure times of the optical spectrometer, a plurality of pixel values, each pixel value corresponding to an electrical response, to an optical spectrum of the reflected light, of a respective one of a plurality of pixels of a color-image sensor. Step 916 is one example of step 616 of method 610.

Figure 10:
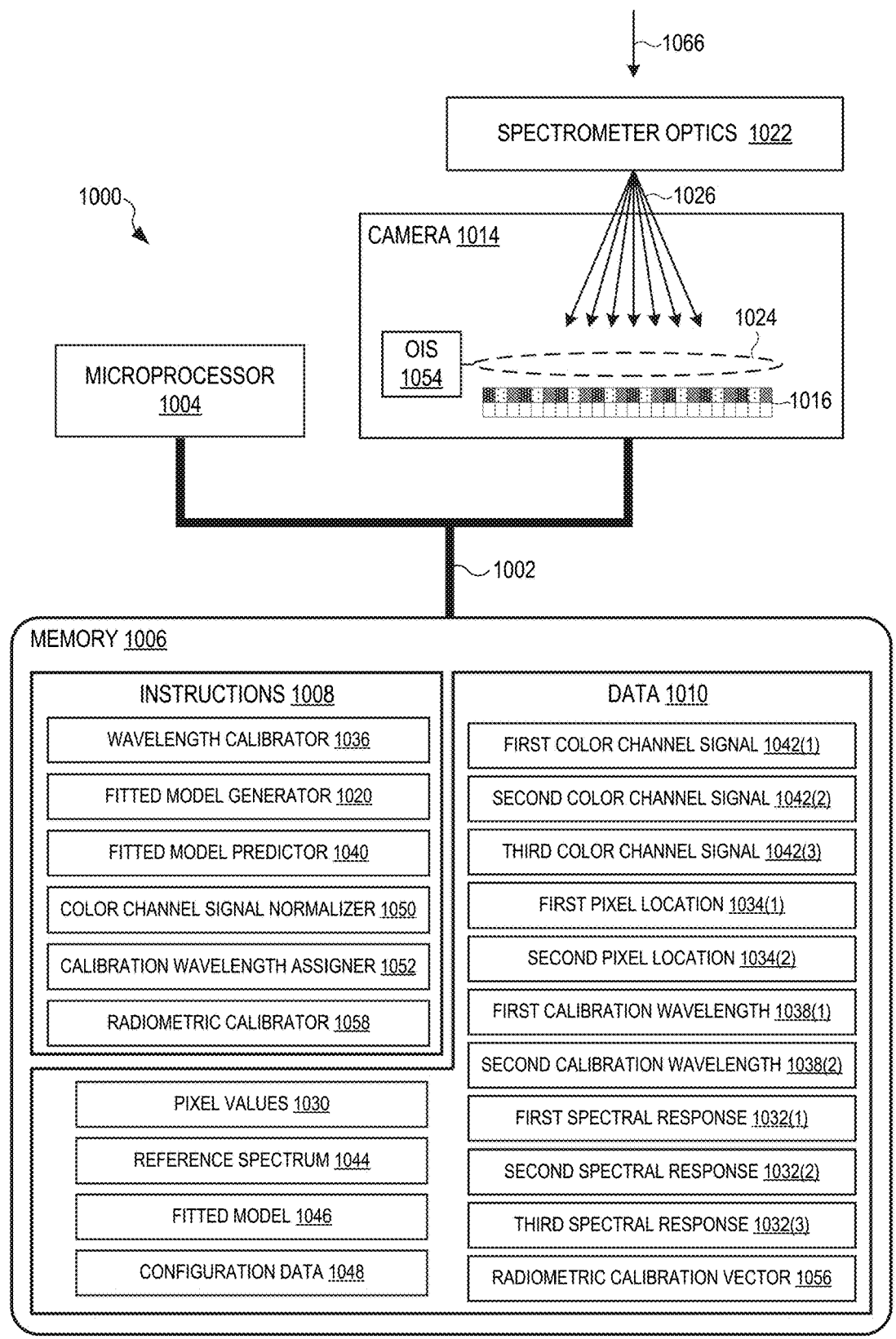
FIG. 10 is a schematic diagram of a spectrum recording system, in embodiments.

FIG. 10 is a schematic diagram of a spectrum recording system 1000. Spectrum recording system 1000 includes a microprocessor circuit 1004 that processes data, a memory 1006 that stores data 1010 and instructions 1008, and a camera 1014 having a color-image sensor 1016 with a plurality of pixels. Microprocessor circuit 1004, memory 1006, camera 1014, and other components of spectrum recording system 1000 are communicatively coupled via a bus 1002. Spectrum recording system 1000 may be part of a smartphone (e.g., smartphone 204 of FIG. 2), tablet computer, laptop computer device, or any other computing device having, or communicatively coupled to, a digital camera. Alternatively, spectrum recording system 1000 may be part of a digital SLR camera, point-and-shoot camera, mirrorless interchangeable lens camera, or other type of digital camera containing memory and a microprocessor circuit. Camera 220 of FIG. 2 is one example of camera 1014, and color-image sensor 100 of FIG. 1 is one example of color-image sensor 1016.

Color-image sensor 1016 includes a color filter array having three types of color filter elements such that each pixel of color-image sensor 1016 has one of a first spectral response, a second spectral response, and a third spectral response, depending upon the color filter type disposed over the pixel. For example, color-image sensor 1016 may include Bayer filter 101 of FIG. 1, wherein the first, second, and third spectral responses are peaked at red, green, and blue, respectively. Color-image sensor 1016 may alternatively be configured with a RGBE filter array, a CYYM filter array, a CYGM filter array, or other type of color filter array, in which case the color filter array of color-image sensor 1016 may have four or more types of color filters in its submosaic.

In some embodiments, spectrum recording system 1000 includes spectrometer optics 1022 that generate an optical spectrum 1026 from an input light 1066 and project optical spectrum 1026 onto color-image sensor 1016. Spectrometer optics 202 of FIG. 2 is one example of spectrometer optics 1022. In other embodiments, camera 1014 includes an OIS 1054 configured to move lens 1024 so as to vary an optical path length between lens 1024 and color-image sensor 1016. Camera 1014 may also include read-out electronics (not shown in FIG. 10) that digitize a photocurrent outputted by each pixel of color-image sensor 1016. In another embodiment, spectrometer optics 1022 are configured to receive a reflected light from an object as input light 1066. The object may be a work of art, a textile, or paint.

Microprocessor circuit 1004 may include at least one central processing unit (CPU), graphics processing unit (GPU), digital signal processor (DSP), field-programmable gate array (FPGA), or other type of integrated circuit capable of performing logic, control, and input/output operations. Microprocessor circuit 1004 may include a mixed-signal integrated circuit, such as a System-on-Chip (SoC) or microcontroller unit (MCU), that combines a processor, memory, and input/output interfaces on a single chip. Microprocessor circuit 1004 may also include a memory controller, bus controller, graphics processing unit, and/or other components that manage data flow between microprocessor circuit 1004, memory 1006, camera 1014, and other components communicatively coupled with bus 1002.

Memory 1006 may include both volatile memory (e.g., RAM, SRAM, etc.) and nonvolatile memory (e.g., ROM, FLASH, etc.). Instructions 1008 include machine-readable instructions that, when executed by microprocessor circuit 1004, control operation of spectrum recording system 1000. As shown in FIG. 10, instructions 1008 include a wavelength calibrator 1036, a fitted model generator 1020, a fitted model predictor 1040, a color channel signal normalizer 1050, a calibration wavelength assigner 1052, and a radiometric calibrator 1058. However, instructions 1008 may include additional instructions (e.g., algorithms, applications, firmware, etc.), as needed to implement functionality of spectrum recording system 1000.

In FIG. 10, data 1010 stored in memory 1006 includes a first color channel signal 1042(1), a second color channel signal 1042(2), a third color channel signal 1042(3), a first pixel location 1034(1), a second pixel location 1034(2), a first calibration wavelength 1038(1), a second calibration wavelength 1038(2), a first spectral response 1032(1), a second spectral response 1032(2), a third spectral response 1032(3), a radiometric calibration vector 1056, pixel values 1030, a reference spectrum 1044, a fitted model 1046, and configuration data 1048. Configuration data 1048 may include values that define operation of instructions 1008. Spectral responses 1032 may include normalized and/or non-normalized spectral responses, and color channel signals 1042 may include normalized and/or non-normalized color channel signals. Although not shown in FIG. 10, data 1010 may include additional data used by instructions 1008 to implement functionality of spectrum recording system 1000.

Instructions 1008 may be configured to control microprocessor circuit 1004 to store one pixel value for each pixel of color-image sensor 1016 as pixel values 1030, each of pixel values 1030 representing an electrical response of a corresponding pixel to optical spectrum 1026. That is, instructions 1008 are configured to control microprocessor circuit 1004 to capture an image with camera 1014 and store the image in memory 1006 as pixel values 1030. In one embodiment, instructions 1008 are configured to control microprocessor circuit 1004 to store pixel values 1030 in a raw image format (e.g., Adobe Digital Negative file) such that no demosaicing, color filter array interpolation or color reconstruction has been applied to pixel values 1030.

Instructions 1008 may be configured to control microprocessor circuit 1004 to form first, second, and third color channel signals 1042 from pixel values 1030 obtained from the pixels having respective first, second, and third spectral responses 1032. In an embodiment where color-image sensor 1016 includes a Bayer filter, instructions 1008 may be configured to control microprocessor circuit 1004 to form red, green, and blue color channel signals from the pixel values obtained from the pixels of color-image sensor 1016 having red-peaked, green-peaked, and blue-peaked spectral responses, respectively.

Wavelength calibrator 1036 may be configured to control microprocessor circuit 1004 to (i) determine first pixel location 1034(1) where first color channel signal 1042(1) equals second color channel signal 1042(2), and (ii) determine second pixel location 1034(2) where second color channel signal 1042(2) equals third color channel signal 1042(3). In one embodiment, color channel signal normalizer 1050 is configured to control microprocessor circuit 1004 to normalize color channel signals 1042 into normalized color channel signals; in this embodiment, wavelength calibrator 1036 may be configured to control microprocessor circuit 1004 to determine first pixel location 1034(1) where normalized first color channel signal 1042(1) equals normalized second color channel signal 1042(2), and determine second pixel location 1034(2) where normalized second color channel signal 1042(2) equals normalized third color channel signal 1042(3).

Wavelength calibrator 1036 may be configured to control microprocessor circuit 1004 to associate first pixel location 1034(1) with first calibration wavelength 1038(1), and second pixel location 1034(2) with second calibration wavelength 1038(2). In one embodiment, wavelength calibrator 1036 is configured to control microprocessor circuit 1004 to (i) store first, second, and third relative spectral responses of color-image sensor 1016 in memory 1006, (ii) store reference spectrum 1044 in memory 1006, (iii) calculate first spectral response 1032(1) from reference spectrum 1044 and the first relative spectral response, (iv) calculate second spectral response 1032(2) from reference spectrum 1044 and the second relative spectral response, (v) calculate third spectral response 1032(3) from reference spectrum 1044 and the third relative spectral response, (vi) identify first calibration wavelength 1038(1) where first spectral response 1032(1) equals second spectral response 1032(2), and (vii) identify second calibration wavelength 1038(2) where the second spectral response 1032(2) equals third spectral response 1032(3).

In some embodiments, fitted model generator 1020 is configured to control microprocessor circuit 1004 to fit pixel locations 1034 and calibration wavelengths 1038 into fitted model 1046. In other embodiments, fitted model predictor 1036 is configured to control microprocessor circuit 1004 to derive from fitted model 1036 a third pixel location for a third wavelength. Fitted model generator 1020 may be configured to control microprocessor circuit 1004 to store fitted model 1046, including the third pixel location and third wavelength, in memory 1006. In one of these embodiments, fitted model generator 1020 is configured to control microprocessor circuit 1004 to generate a linear model 1046 (e.g., apply linear regression to pixel locations 1034 and calibration wavelengths 1038). In one embodiment, calibration wavelength assigner 1052 is configured to control microprocessor circuit 1004 to use fitted model 1046 to assign one wavelength to each pixel position of color-image sensor 1016. In some embodiments, radiometric calibrator 1058 is configured to control microprocessor circuit 1004 to compare pixel values 1030 to reference spectrum 1044 to generate radiometric calibration vector 1056.

Figure 11:
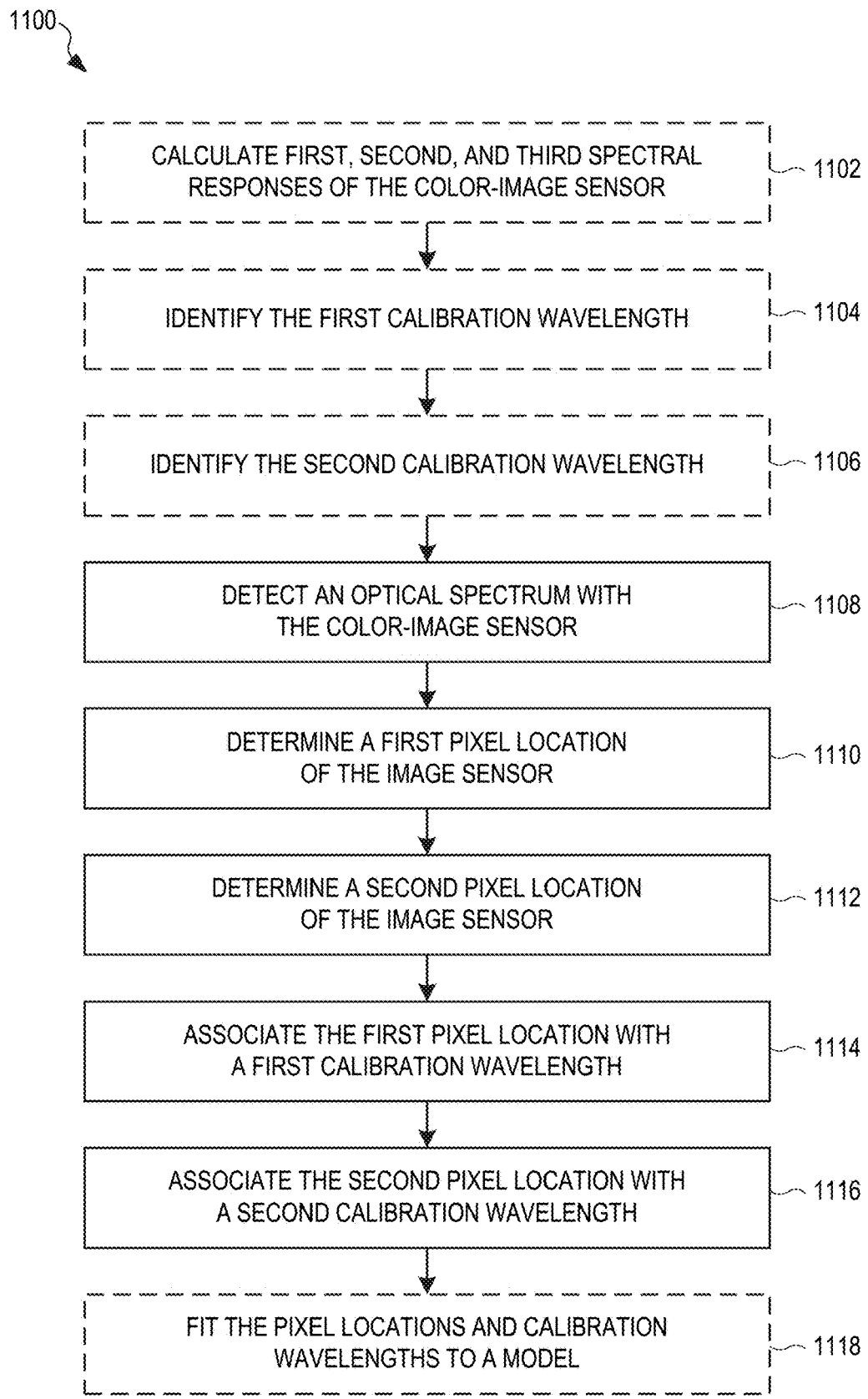
FIG. 11 is a flowchart illustrating one example method that calibrates a color-image sensor for optical spectrometry, in embodiments.

FIG. 11 is a flowchart illustrating one example method 1100 that calibrates a color-image sensor for optical spectrometry. Method 1100 includes a step 1108 that detects an optical spectrum with the color-image sensor, the color-image sensor having an image sensor overlaid with a color filter array such that each of a plurality of pixels of the color-image sensor has one of a first spectral response, a second spectral response, and a third spectral response. In one example of step 1108, instructions 1008 of spectrum recording system 1000 control microprocessor circuit 1004 to store pixel values 1030 in memory 1006.

Method 1100 also includes a step 1110 that determines a first pixel location of the color-image sensor where a first color channel signal, formed from the pixels having the first spectral response, equals a second color channel signal formed from the pixels having the second spectral response. Method 1100 also includes a step 1112 that determines a second pixel location of the color-image sensor where the second color channel signal equals a third color channel signal formed from the pixels having the third spectral response. In one example of steps 1110 and 1112, instructions 1008 of spectrum recording system 1000 control microprocessor circuit 1004 to (i) form first color channel signal 1042(1), second color channel signal 1042(2), and third color channel signal 1042(3) from pixel values 1030 obtained from the pixels having first spectral response 1032(1), second spectral response 1032(2), and third spectral response 1032(3), respectively, (ii) determine first pixel location 1034(1) where first color channel signal 1042(1) equals second color channel signal 1042(2), and (iii) determine second pixel location 1034(2) where second color channel signal 1042(2) equals third color channel signal 1042(3).

Method 1100 also includes a step 1114 that associates the first pixel location with a first calibration wavelength, and a step 1116 that associates the second pixel location with a second calibration wavelength. In one example of steps 1114 and 1116, wavelength calibrator 1036 of spectrum recording system 1000 controls microprocessor circuit 1004 to (i) associate first pixel location 1034(1) with first calibration wavelength 1038(1), and (ii) associate second pixel location 1034(2) with second calibration wavelength 1038(2).

In one embodiment, method 1100 includes a step 1118 that fits the first pixel location, first calibration wavelength, second pixel location, and second calibration wavelength to associate a third pixel location of the color-image sensor with a third wavelength. In one example of step 1118, fitted model generator 1020 of spectrum recording system 1000 controls microprocessor circuit 1004 to fit pixel locations 1034 and calibration wavelengths 1038 into fitted model 1046. Furthermore, fitted model predictor 1036 controls microprocessor circuit 1004 to derive from fitted model 1046 a third pixel location for a third wavelength.

In another embodiment, method 1100 includes a step 1102 that calculates the first, second, and third spectral responses of the color-image sensor, a step 1104 that identifies the first calibration wavelength where the first spectral response equals the second spectral response, and a step 1106 that identifies the second calibration wavelength where the second spectral response equals the third spectral response. In one example of steps 1102, 1104, and 1106, instructions 1008 of spectrum recording system 1000 control microprocessor circuit 1004 to (i) calculate first spectral response 1032(1) from reference spectrum 1044 and the first relative spectral response, (ii) calculate second spectral response 1032(2) from reference spectrum 1044 and the second relative spectral response, (iii) calculate third spectral response 1032(3) from reference spectrum 1044 and the third relative spectral response, (iv) identify first calibration wavelength 1038(1) where first spectral response 1032(1) equals second spectral response 1032(2), and (v) identify second calibration wavelength 1038(2) where second spectral response 1032(2) equals third spectral response 1032(3).

In some embodiments, step 1108 of method 1100 detects the optical spectrum with steps that (i) receive an input light with spectrometer optics that project the optical spectrum of the input light onto the color-image sensor, and (ii) record, for each of the pixels, one pixel value representing an electrical response of said each of the pixels to the optical spectrum. In one of these embodiments, the step that receives the input light includes a step that positions the spectrometer optics and color-image sensor to receive reflected light from an object. In another embodiment, method 1100 includes a step that illuminates the object with a source light that reflects off of the object to create the reflected light. The object may be a work of art, a textile, or paint.

Figure 12:
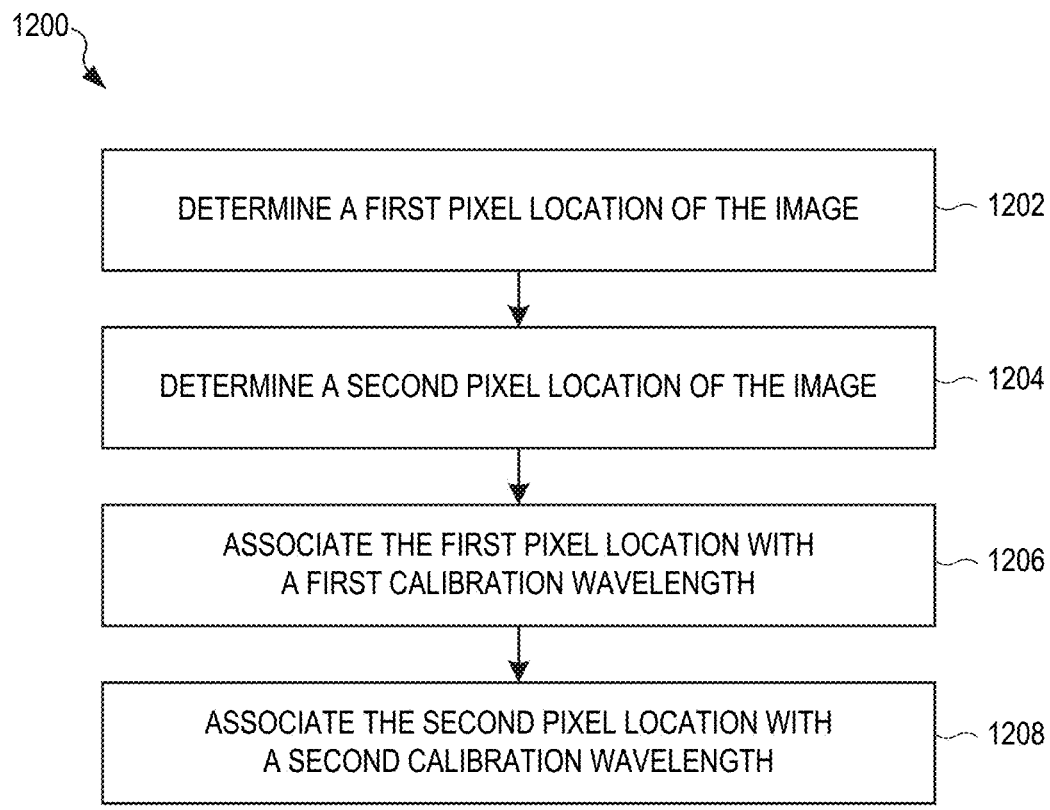
FIG. 12 is a flowchart illustrating one example method that calibrates an image of an optical spectrum obtained with an optical spectrometer, in embodiments.

FIG. 12 is a flowchart illustrating one example method 1200 that calibrates an image of an optical spectrum obtained with an optical spectrometer. Method 1200 includes a step 1202 that determines a first pixel location of the image where a first color channel signal of the image equals a second color channel signal of the image. Method 1200 also includes a step 1204 that determines a second pixel location of the image where the second color channel signal equals a third color channel signal of the image. In one example of steps 1202 and 1204, wavelength calibrator 1036 of spectrum recording system 1000 controls microprocessor circuit 1004 to (i) determine first pixel location 1034(1) where first color channel signal 1042(1) equals second color channel signal 1042(2), and (ii) determine second pixel location 1034(2) where second color channel signal 1042(2) equals third color channel signal 1042(3).

Method 1200 also includes a step 1206 that associates the first pixel location with a first calibration wavelength, and a step 1208 that associates the second pixel location with a second calibration wavelength. In one example of steps 1202 and 1204, wavelength calibrator 1036 of spectrum recording system 1000 controls microprocessor circuit 1004 to (i) associate first pixel location 1034(1) with first calibration wavelength 1038(1), and (ii) associate second pixel location 1034(2) with second calibration wavelength 1038(2).

In some embodiments, color-image sensor 100 includes a color filter array having four types of color filters, such as a RGBE filter array, a CYYM filter array, or a CYGM filter array. In these embodiments, some of the pixels of color-image sensor 100 have a fourth spectral response. Pixel values derived from pixels having the fourth spectral response may be grouped so as to form a fourth color channel signal. A third pixel location of the color-image sensor, where the third color channel signal equals the fourth color channel signal, may be determined. The third pixel location may be associated with a third reference wavelength. In one of these embodiments, the three pixel locations and three calibration wavelengths may be fitted to a model used to associate a fourth pixel location of color-image sensor 100 to a fourth wavelength. In another of these embodiments, the fourth calibration wavelength is determined where the third spectral response equals the fourth spectral response.

In some embodiments, color-image sensor 100 includes a color filter array having several types of color filters (e.g., five or more), each color filter types having one spectral response. All pixel values derived from pixels having the same spectral response may be grouped together to form a corresponding color channel signal. Where one color channel signal equals another color channel signal, a corresponding calibration wavelength may be determined. Furthermore, it should be appreciated that a spectral response having a broad bandwidth may equal another spectral response at a plurality of calibration wavelengths. The two corresponding color channel signals may cross at a plurality of pixel positions, up to a number of the plurality of calibration wavelengths. Each of the plurality of pixel positions may be associated with one of the plurality of calibration wavelengths. The plurality of pixel positions and associated calibration wavelengths may then be included in fitting to generate the fitted model.

Figure 13:
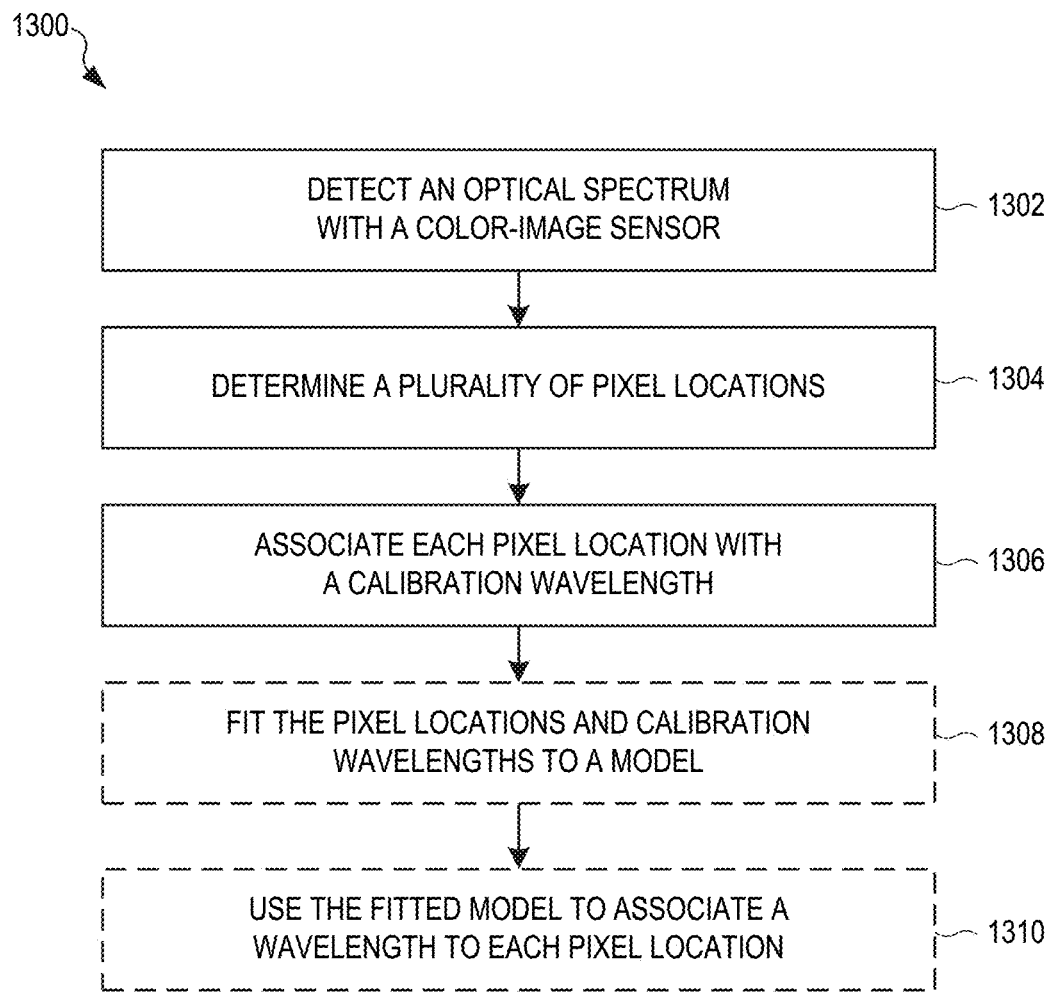
FIG. 13 is a flowchart illustrating another example method that calibrates a color-image sensor for optical spectrometry, in embodiments.

FIG. 13 is a flowchart illustrating another example method 1300 that calibrates a color-image sensor for optical spectrometry. Method 1300 includes a step 1302 that detects an optical spectrum with the color-image sensor, the color-image sensor having an image sensor overlaid with a color pixel array such that each of a plurality of pixels of the color-image sensor has one of several spectral responses. Step 1108 of method 1100 is one example of method 1300, wherein each of the plurality of pixels of the color-image sensor has one of three spectral responses (e.g., red, green, and blue). Method 1300 also includes a step 1304 that determines a plurality of pixel locations of the color-image sensor where, for each of the pixel locations, a color channel signal formed from pixels having one spectral response equals a second color channel signal formed from pixels having another spectral response. Steps 1110 and 1112 of method 1100 are examples of step 1304. Method 1300 also includes a step 1306 that associates each of the pixel locations with a calibration wavelength. Steps 1114 and 1116 of method 1100 are examples of step 1306.

In some embodiments, method 1300 includes a step 1308 that fits the pixel locations and calibration wavelengths to a model. The model may be a linear model obtained, for example, by linear regression. Step 1118 of method 1100 is one example of step 1308. In other embodiments, method 1300 includes a step 1310 that uses the fitted model to associate a wavelength to each of the pixel locations.

In the above discussion, any color-image sensor and/or color filter array may operate outside of the visible spectrum, such as the infrared (e.g., near, mid, and far) and ultraviolet regions of the electromagnetic spectrum.

Changes may be made in the above methods and systems without departing from the scope hereof. It should thus be noted that the matter contained in the above description or shown in the accompanying drawings should be interpreted as illustrative and not in a limiting sense. Herein, and unless otherwise indicated, the adjective "exemplary" means serving as an example, instance, or illustration. The following claims are intended to cover all generic and specific features described herein, as well as all statements of the scope of the present method and system, which, as a matter of language, might be said to fall therebetween.

What is claimed is:

1. A method that calibrates a color-image sensor for optical spectrometry, comprising:
    detecting an optical spectrum with the color-image sensor, the color-image sensor having an image sensor overlaid with a color filter array such that each of a plurality of pixels of the color-image sensor has one of several spectral responses;
    determining a plurality of pixel locations of the color-image sensor where, for each of the pixel locations, a color channel signal formed from pixels having one spectral response equals a second color channel signal formed from pixels having another spectral response; and
    associating each of the pixel locations with a calibration wavelength.

2. A method that calibrates a color-image sensor for optical spectrometry, comprising:
    detecting an optical spectrum with the color-image sensor, the color-image sensor having an image sensor overlaid with a color filter array such that each of a plurality of pixels of the color-image sensor has one of a first spectral response, a second spectral response, and a third spectral response;
    determining a first pixel location of the color-image sensor where a first color channel signal, formed from the pixels having the first spectral response, equals a second color channel signal formed from the pixels having the second spectral response;
    determining a second pixel location of the color-image sensor where the second color channel signal equals a third color channel signal formed from the pixels having the third spectral response;
    associating the first pixel location with a first calibration wavelength; and
    associating the second pixel location with a second calibration wavelength.

3. The method of claim 2, further comprising fitting the first pixel location, first calibration wavelength, second pixel location, and second calibration wavelength to associate a third pixel location of the color-image sensor with a third wavelength.

4. The method of claim 3, wherein fitting comprises linearly fitting.

5. The method of claim 3, further comprising comparing the detected optical spectrum with an expected spectrum to radiometrically calibrate the first, second, and third color channel signals.

6. The method of claim 2, further comprising:
    identifying the first calibration wavelength where the first spectral response equals the second spectral response; and
    identifying the second calibration wavelength where the second spectral response equals the third spectral response.

7. The method of claim 6,
    further comprising normalizing the first, second, and third color channel signals of the color-image sensor into normalized first, second, and third color channel signals, respectively;
    wherein:
        determining the first pixel location of the color-image sensor includes determining the first pixel location where the normalized first color signal equals the normalized second color channel signal; and
        determining the second pixel location of the color-image sensor includes determining the second pixel location where the normalized second color channel signal equals the normalized third color channel signal.

8. The method of claim 7, wherein:
    determining the first pixel location of the color-image sensor includes determining the first pixel location where the normalized first color channel signal and the normalized second color channel signal cross; and
    determining the second pixel location of the color-image sensor includes determining the second pixel location where the normalized second color channel signal and the normalized third color channel signal cross.

9. The method of claim 8, further comprising:
    measuring a first relative spectral response of the color-image sensor, a second relative spectral response of the color-image sensor, and a third relative spectral response of the color-image sensor;
    obtaining a reference spectrum;
    calculating the first spectral response from the reference spectrum and the first relative spectral response;
    calculating the second spectral response from the reference spectrum and the second relative spectral response; and
    calculating the third spectral response from the reference spectrum and the third relative spectral response.

10. The method of claim 6, wherein detecting the optical spectrum includes:
    receiving an input light with spectrometer optics that project the optical spectrum of the input light onto the color-image sensor; and
    recording, for each of the pixels, one pixel value representing an electrical response of said each of the pixels to the optical spectrum.

11. The method of claim 10, wherein receiving the input light includes positioning the spectrometer optics and color-image sensor to receive reflected light from an object.

12. The method of claim 11, further comprising illuminating the object with a source light that reflects off of the object to create the reflected light.

13. The method of claim 12, wherein the object is paint.

14. The method of claim 2,
    wherein detecting the optical spectrum includes detecting the optical spectrum with the color-image sensor having a four-color color filter array such that each of the pixels of the color-image sensor has one of a first spectral response, a second spectral response, a third spectral response, and a fourth spectral response; and
    further including:
        determining a third pixel location of the color-image sensor where the third color channel signal equals a fourth color channel signal formed from the pixels having the fourth spectral response; and
        associating the third pixel location with a third calibration wavelength.

15. The method of claim 14, further comprising fitting the first pixel location, first calibration wavelength, second pixel location, second calibration wavelength, third pixel location, and third calibration wavelength to associate a fourth pixel location of the color-image sensor with a fourth wavelength.

16. The method of claim 14, further comprising identifying the third calibration wavelength where the third spectral response equals the fourth spectral response.

17. A spectrum recording system, comprising:
a color-image sensor formed from an image sensor overlaid with a color filter array such that each of a plurality of pixels of the color-image sensor has one of a first spectral response, a second spectral response, and a third spectral response;
at least one processor;
memory communicatively coupled to the at least one processor and the color-image sensor; and
machine-readable instructions stored in the memory and configured to control the at least one processor to:
   (i) for each of the pixels, store in the memory one pixel value representing an electrical response of said each of the pixels to an optical spectrum detected with the color-image sensor;
   (ii) form a first color channel signal, a second color channel signal, and a third color channel signal from the pixel values obtained from the pixels having the first spectral response, second spectral response, and third spectral response, respectively;
   (iii) determine a first pixel location where the first color channel signal equals the second color channel signal;
   (iv) determine a second pixel location where the second color channel signal equals the third color channel signal;
   (v) associate the first pixel location with a first calibration wavelength; and
   (vi) associate the second pixel location with a second calibration wavelength.

18. The spectrum recording system of claim 17, further comprising machine-readable instructions configured to control the at least one processor to:
   (vii) fit the first pixel location, first calibration wavelength, second pixel location, and second calibration wavelength to a model; and
   (viii) derive from the model a third pixel location for a third wavelength.

19. The spectrum recording system of claim 18, wherein the machine-readable instructions are configured to control the at least one processor to fit the first pixel location, first calibration wavelength, second pixel location and second calibration wavelength to a linear model.

20. The spectrometer of claim 17, wherein the machine-readable instructions are configured to control the at least one processor to store the pixel values in the memory in a raw image format.

21. The spectrum recording system of claim 17,
further comprising machine-readable instructions configured to control the at least one processor to normalize the first, second, and third color channel signals into normalized first, second, and third color channel signals, respectively;
wherein:
   the at least one processor determines the first pixel location where the normalized first color channel signal equals the normalized second color channel signal; and
   the at least one processor determines the second pixel location where the normalized second color channel signal equals the normalized third color channel signal.

22. The spectrum recording system of claim 21, further comprising machine-readable instructions configured to control the at least one processor to:
   (vii) store in the memory a first relative spectral response of the color-image sensor, a second relative spectral response of the color-image sensor, and a third relative spectral response of the color-image sensor;
   (viii) store in the memory a reference spectrum;
   (ix) calculate the first spectral response from the reference spectrum and the first relative spectral response;
   (x) calculate the second spectral response from the reference spectrum and the second relative spectral response;
   (xi) calculate the third spectral response from the reference spectrum and the third relative spectral response;
   (xii) identify the first calibration wavelength where the first spectral response equals the second spectral response; and
   (xiii) identify the second calibration wavelength where the second spectral response equals the third spectral response.

23. The spectrum recording system of claim 22, further comprising machine-readable instructions configured to control the at least one processor to:
   (xiv) compare the pixel values to the reference spectrum to generate a radiometric calibration vector; and
   (xv) store the radiometric calibration vector in the memory.

24. The spectrum recording system of claim 22, further comprising spectrometer optics configured to project an input light onto the color-image sensor as the optical spectrum.

25. The spectrum recording system of claim 24, the spectrometer optics being further configured to receive a reflected light from an object as the input light.

26. The spectrum recording system of claim 25, the object being paint.

* * * * *